(12) United States Patent
Hofeldt

(10) Patent No.: US 9,089,257 B2
(45) Date of Patent: Jul. 28, 2015

(54) BINARY CHOICE SELF-TESTING

(71) Applicant: Albert John Hofeldt, Miami Beach, FL (US)

(72) Inventor: Albert John Hofeldt, Miami Beach, FL (US)

( * ) Notice: Subject to any disclaimer, the term of this patent is extended or adjusted under 35 U.S.C. 154(b) by 95 days.

(21) Appl. No.: 13/944,880

(22) Filed: Jul. 18, 2013

(65) Prior Publication Data

US 2015/0022782 A1    Jan. 22, 2015

Related U.S. Application Data

(60) Provisional application No. 61/741,335, filed on Jul. 18, 2012.

(51) Int. Cl.
*A61B 3/02* (2006.01)
*A61B 3/00* (2006.01)
*A61B 3/032* (2006.01)
*A61B 3/18* (2006.01)
*H05B 37/02* (2006.01)

(52) U.S. Cl.
CPC ............. *A61B 3/0033* (2013.01); *A61B 3/0083* (2013.01); *A61B 3/032* (2013.01); *A61B 3/18* (2013.01); *H05B 37/0209* (2013.01)

(58) Field of Classification Search
CPC .................................. A61B 3/02; A61B 3/18
USPC .................. 351/239, 237, 240, 241, 242, 246
See application file for complete search history.

(56) References Cited

U.S. PATENT DOCUMENTS 5,568,209 A  * 10/1996 Priester et al. ................ 351/243
6,425,665 B2 *  7/2002 Hayashi et al. ............... 351/239

* cited by examiner

*Primary Examiner* — Hung Dang

(57) ABSTRACT

My invention is an automated self-testing method utilizing binary choice, which is applicable to monocular and binocular eye tests and can be administered on computer, cellular phones, and other electronic devices. Binary choice of match or no match, yes or no, present or absence provides simple means of automated testing by stepwise progression through staircase algorisms. Necessary devices have been introduced in order to fully utilize the power of binary choice self testing, such as, (1) printed display overlays for testing fine visual acuity at near, (2) bright illuminator of printed overlays to allow automated potential vision testing, (3) the use of complementary color lenses and color test isopters for binocular perimetry. All the programs are linked together in a multifunction electronic program tailored for Internet applications

9 Claims, 24 Drawing Sheets

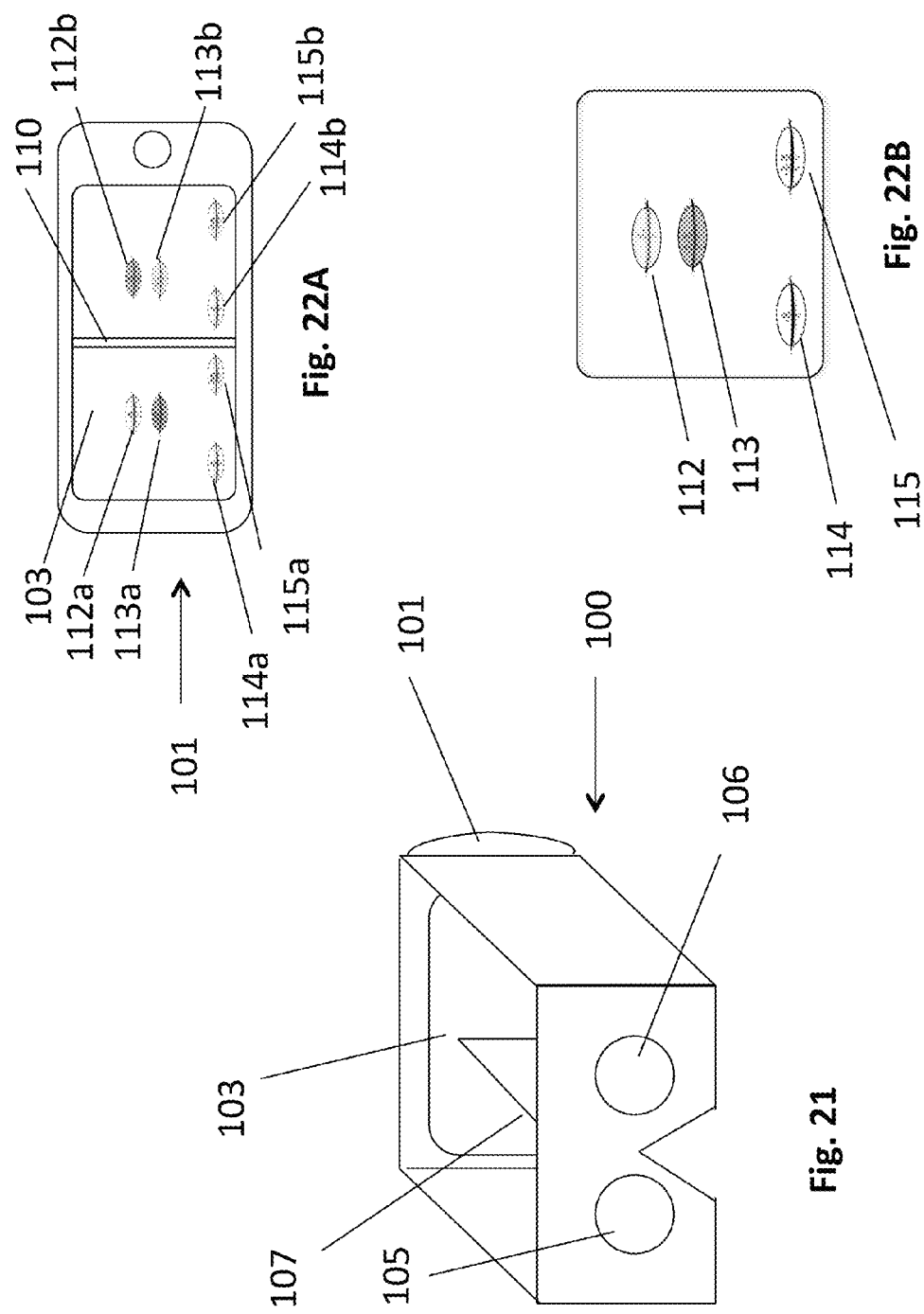

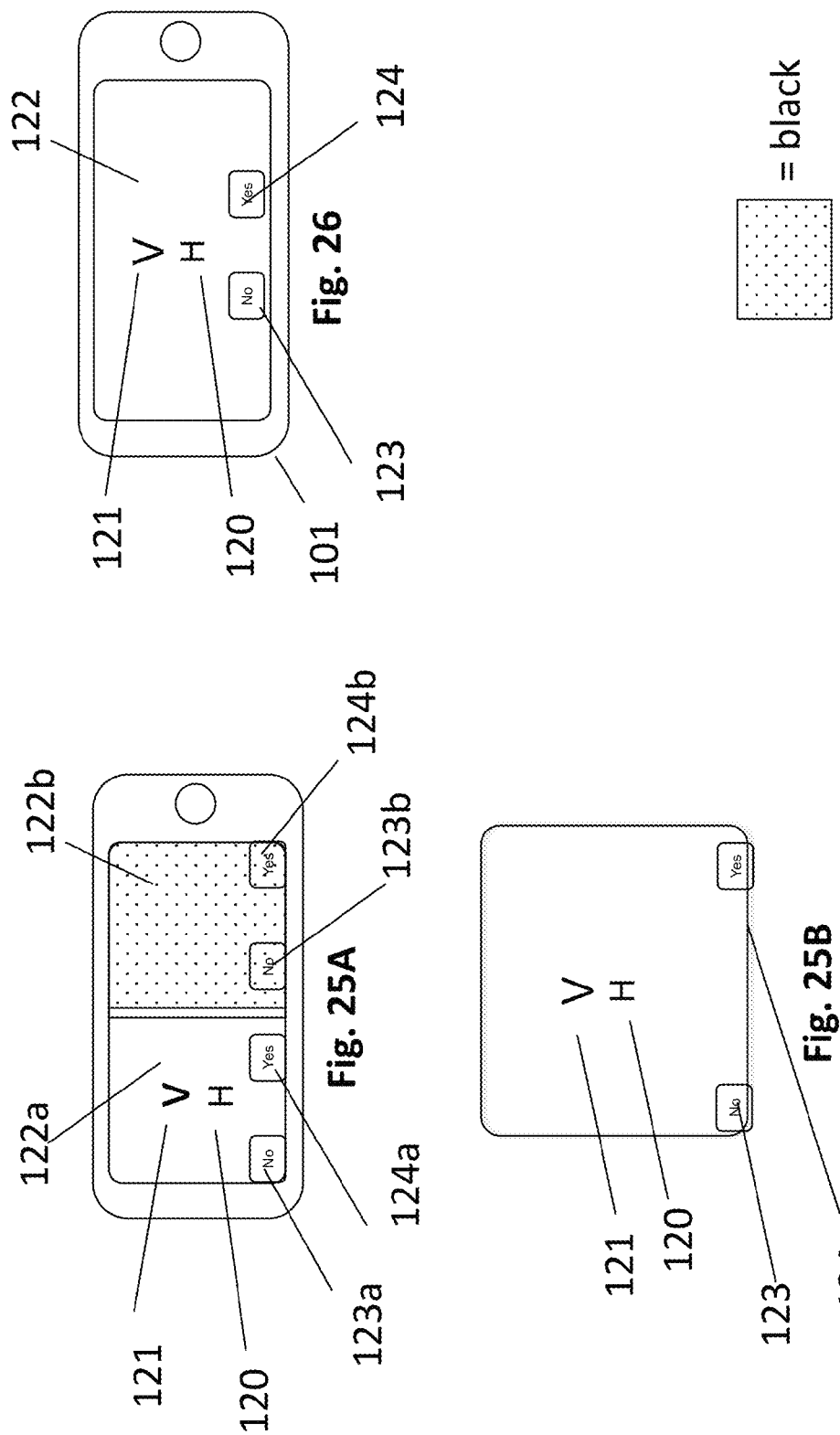

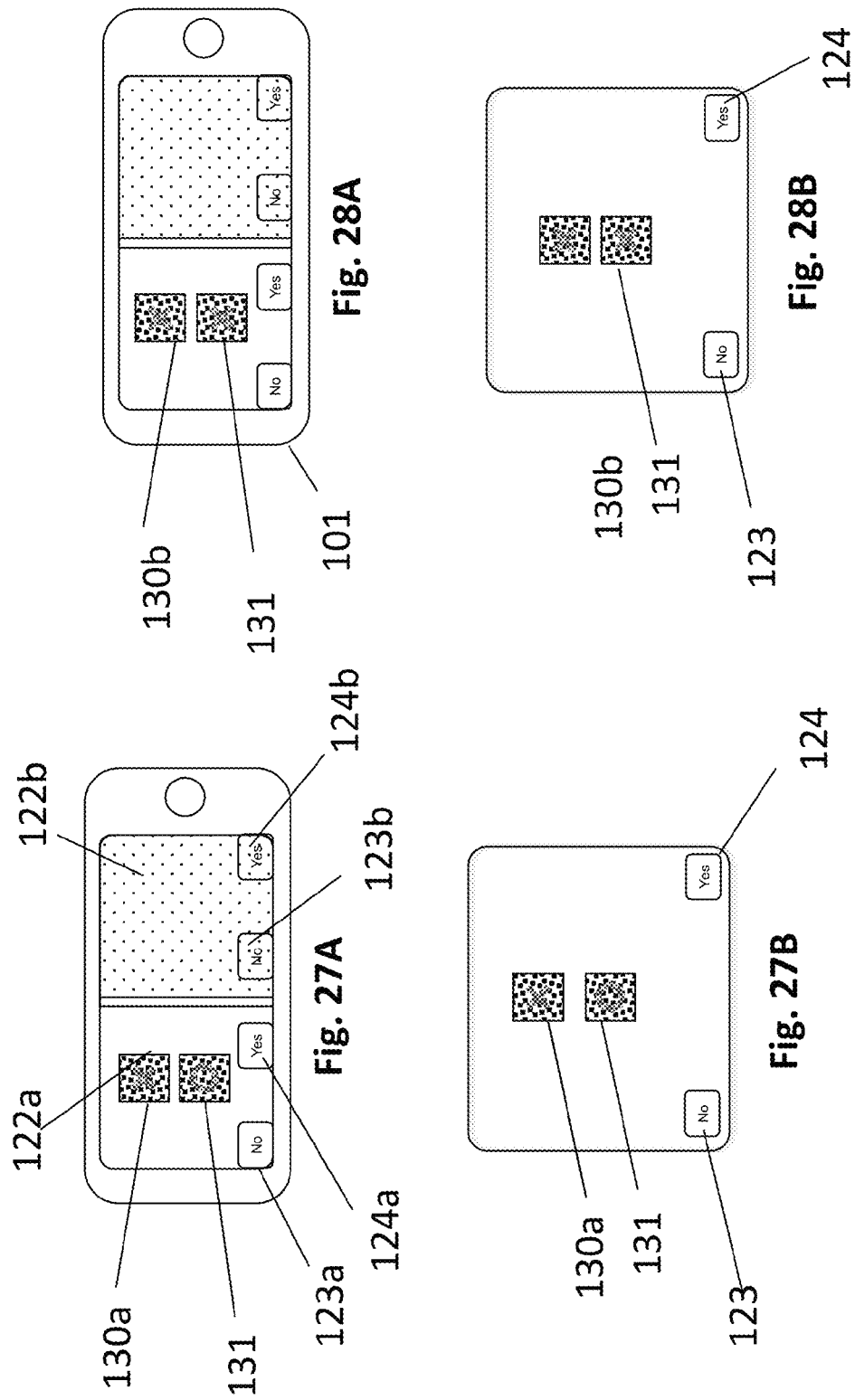

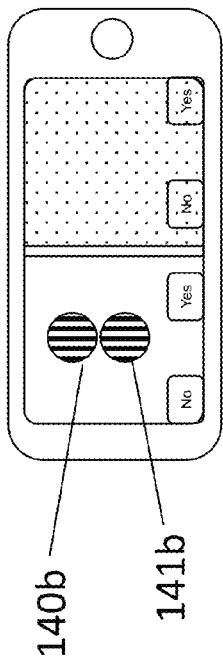
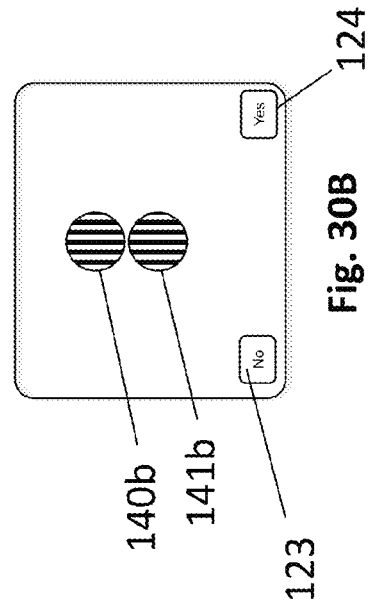
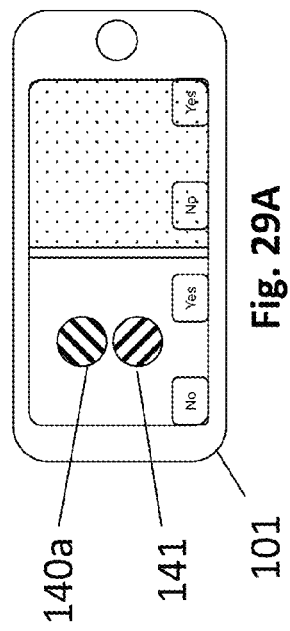
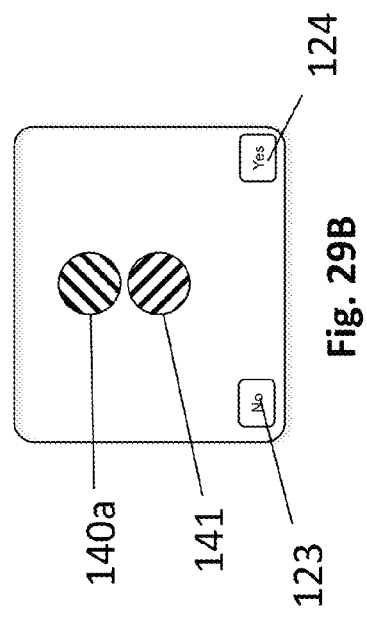

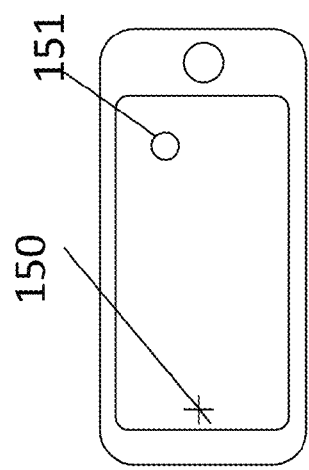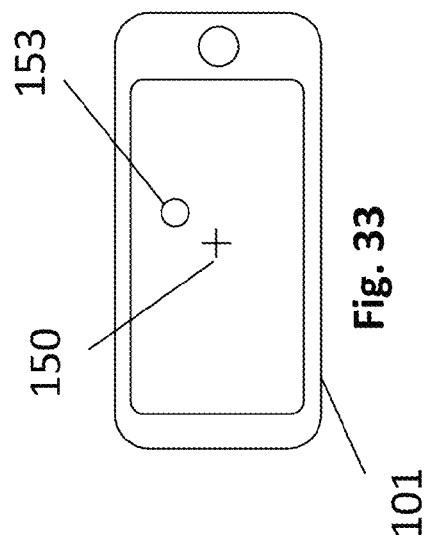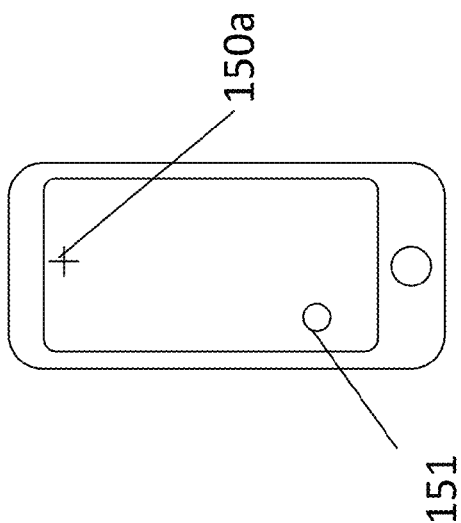

 Blue
 Red
 Black
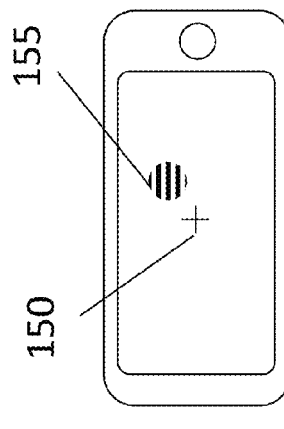
Fig. 36A
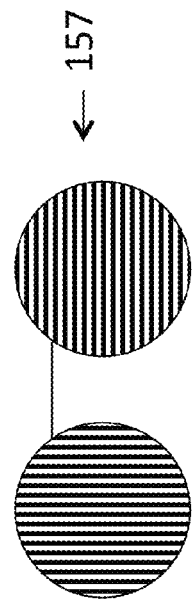
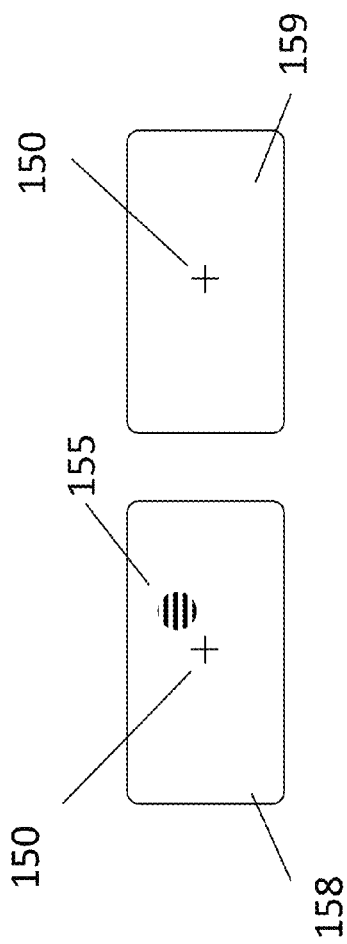
Fig. 36B

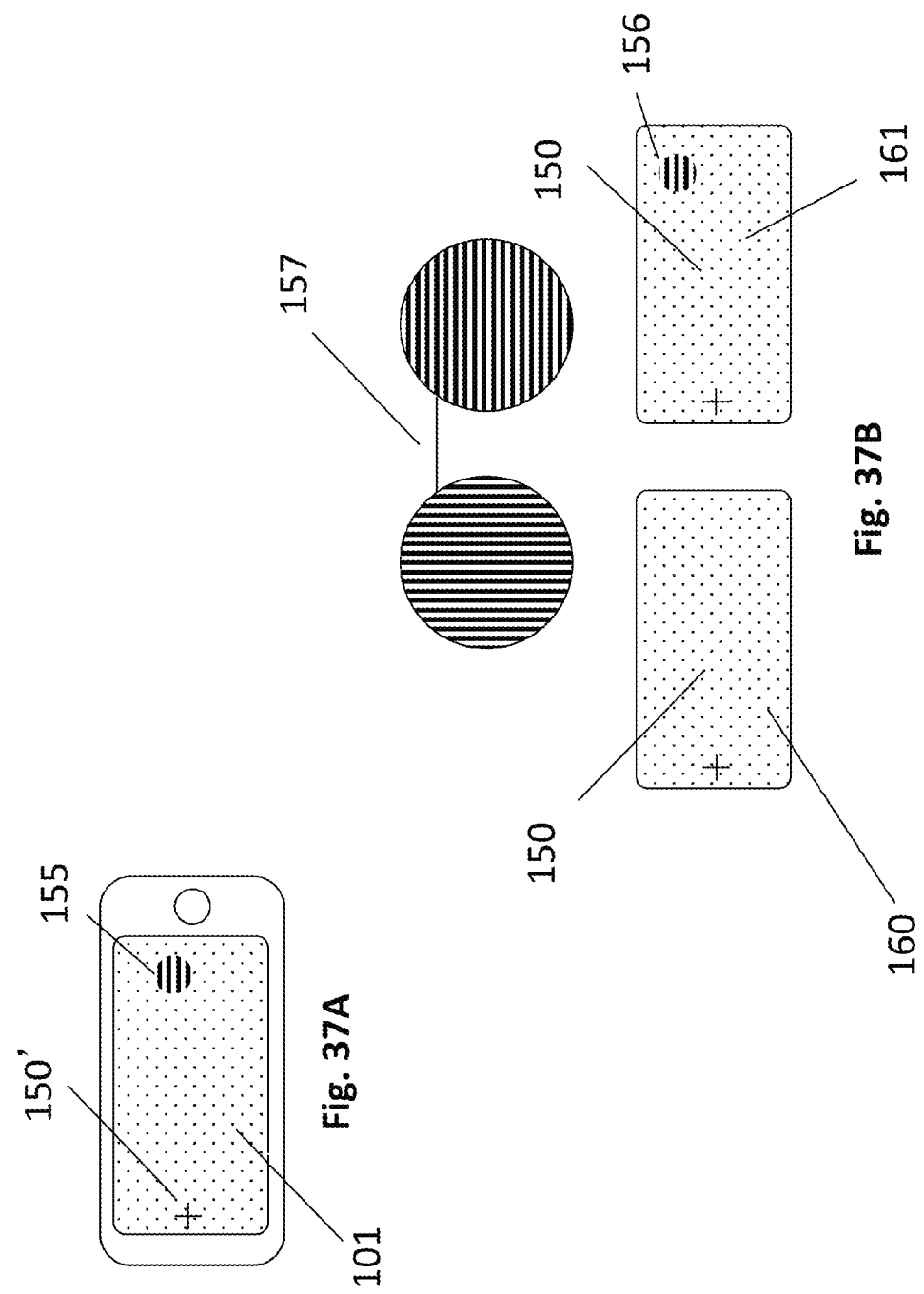

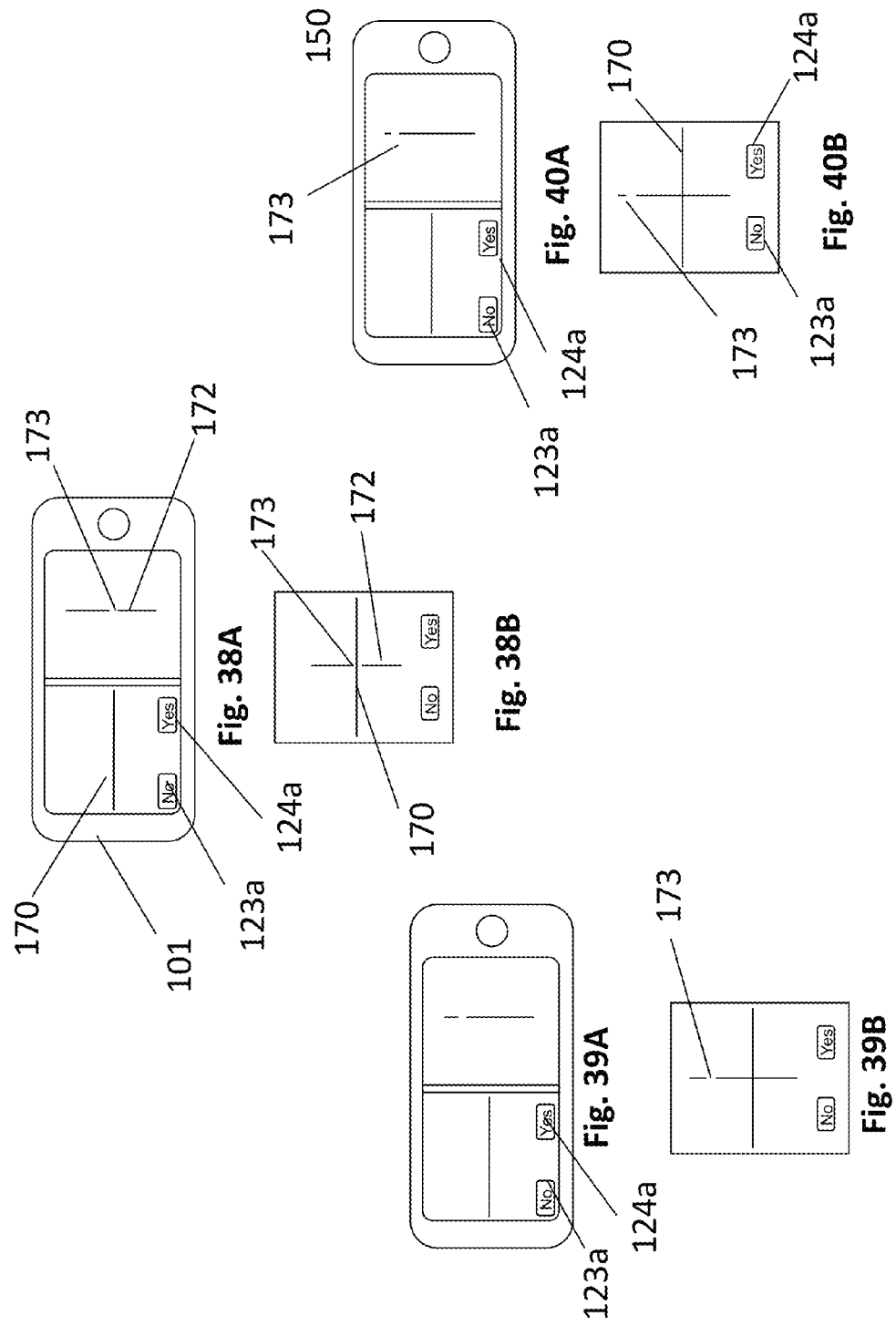

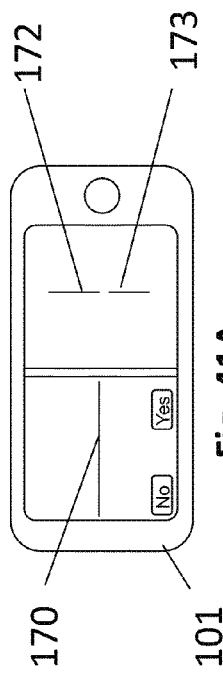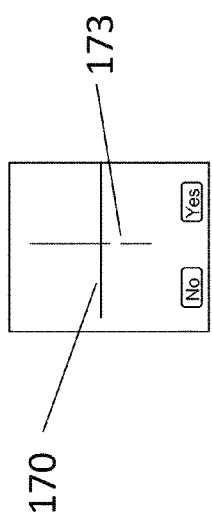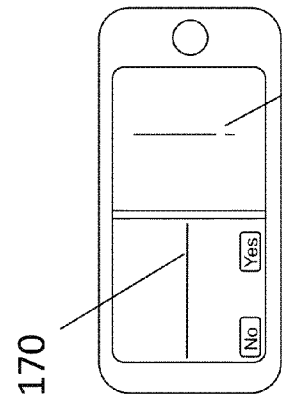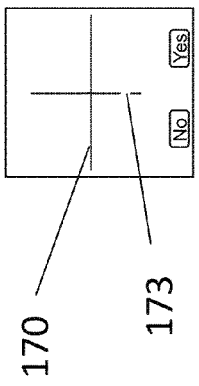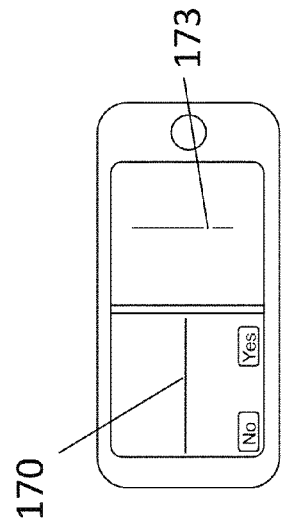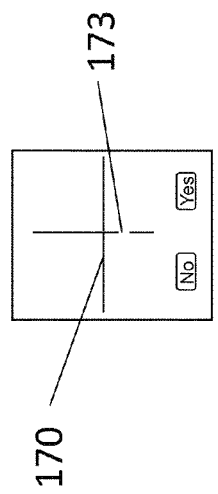

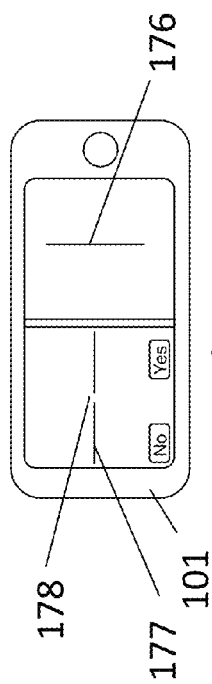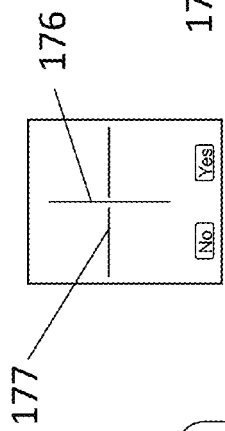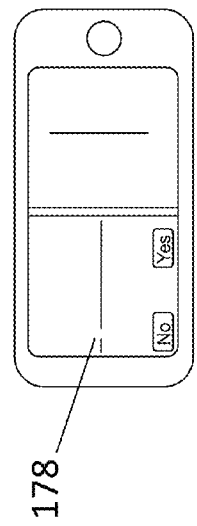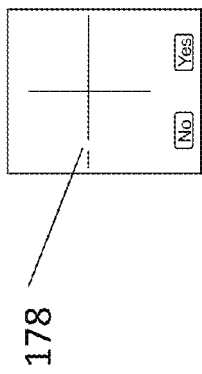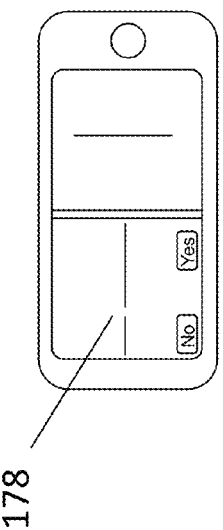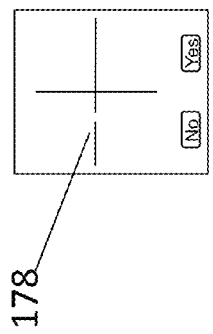

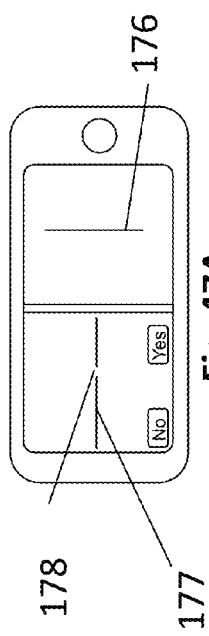
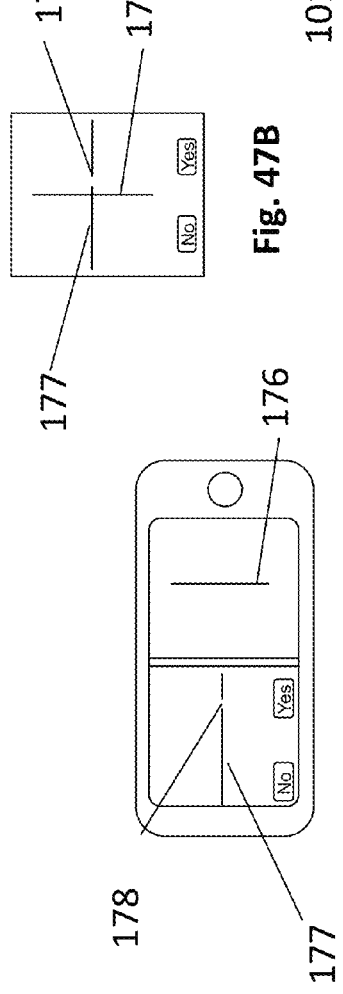
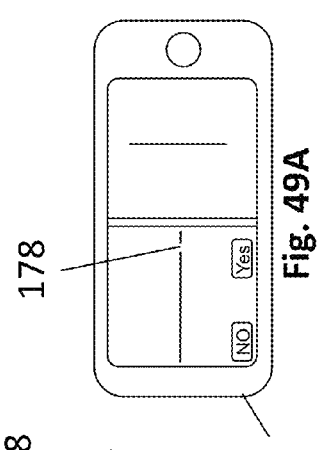
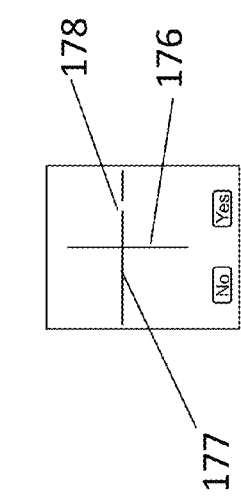
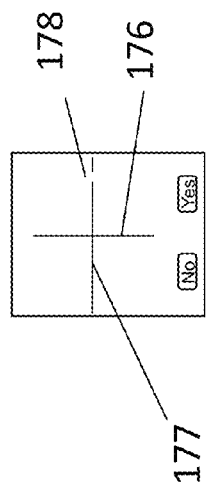

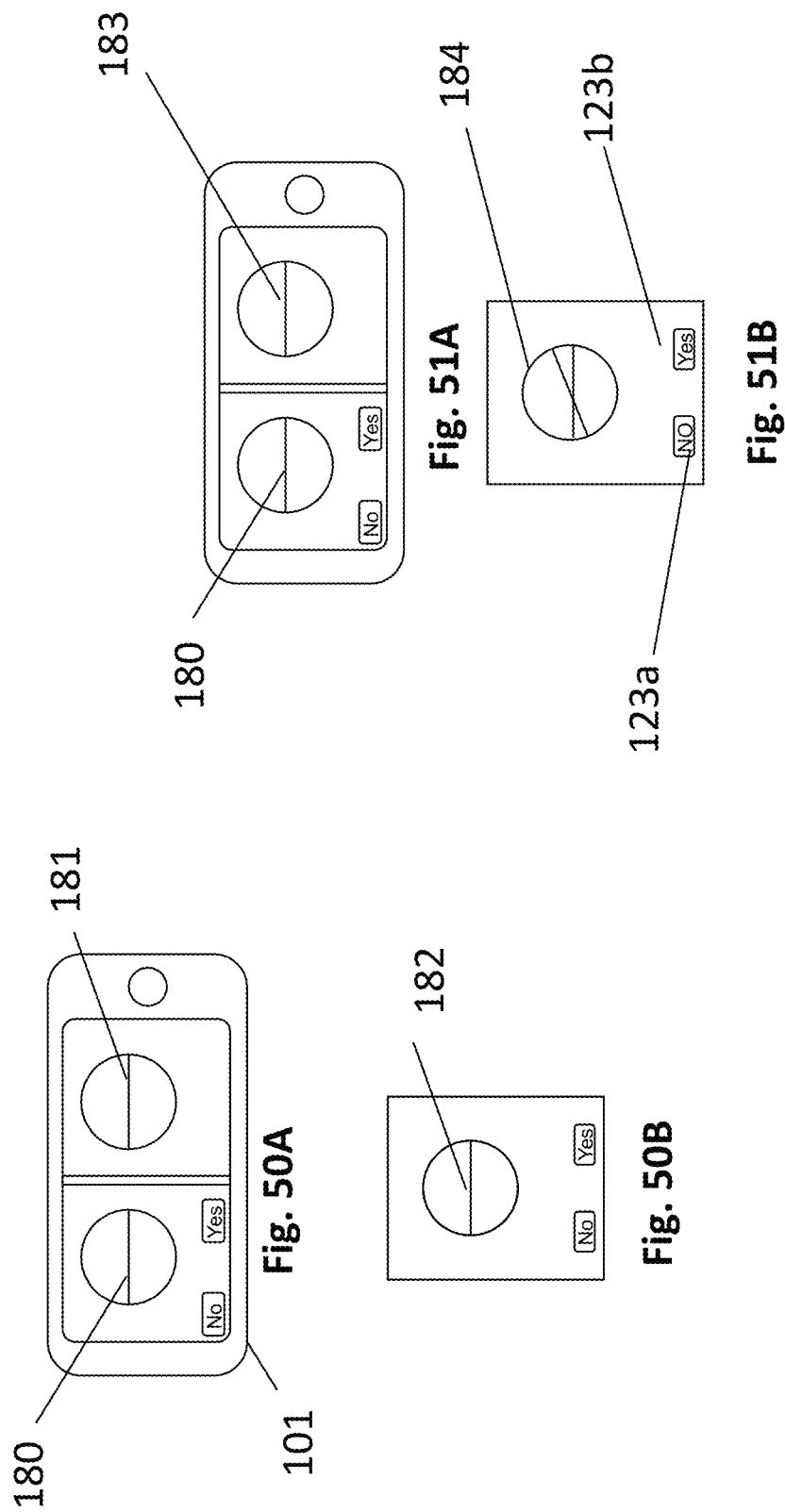

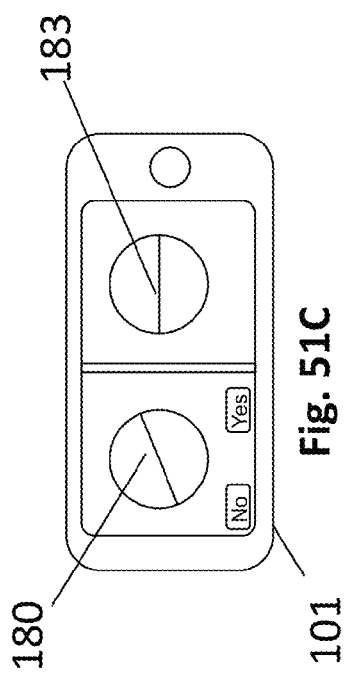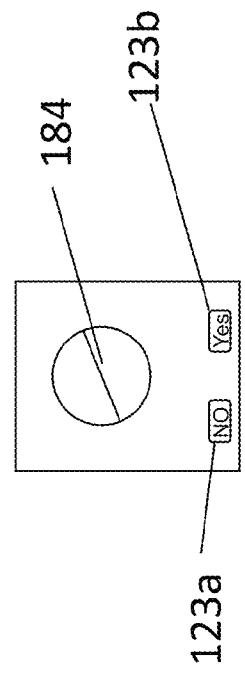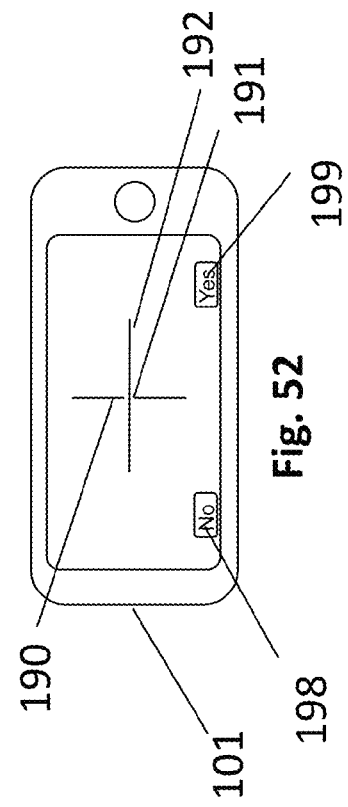

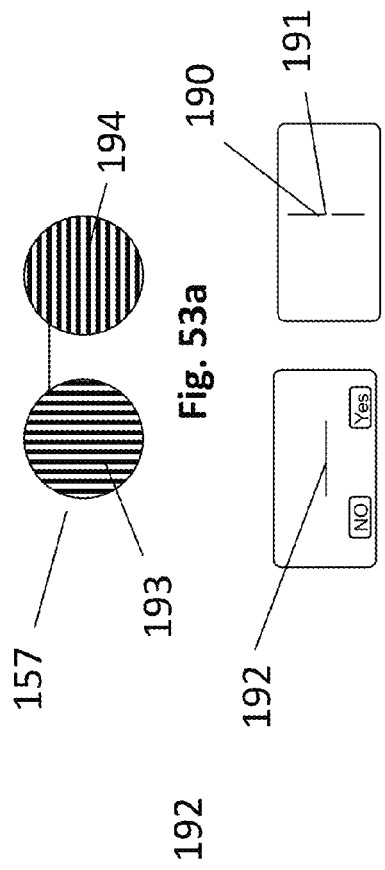

BINARY CHOICE SELF-TESTING

CROSS REFERENCE TO RELATED APPLICATIONS

Provisional patent application 61/741,335 dated Jul. 18, 2012 Binary Vision Test

STATEMENT REGARDING FEDERALLY SPONSORED OR DEVELOPMENT

Not Applicable

DESCRIPTION OF ATTACHED APPENDIX

Not Applicable

BACKGROUND

There are a number of vision test that are controlled by manual or computer driven means. Some vision tests are self-tests in that an operator is not interacting with the subject during testing and a good example of this type of vision test is the automated visual field examination. Currently, visual acuity and other eye tests require a test administor to record the receited answers. Personnel having special training in optics administer most vision tests. With automated testing, vision screening at the primary care level by technicians not specially trained could identify diseases at an early stage, particularly the diabetic patient who is prone to vision threatening complications, complications that can be prevented or ameliorated by early intervention through advance eye care. If acuity and other sensory test were automated, screening at the primary care level would be feasible.

Cellular devices now capable of processing complicated presentation programs such as Keynote for Apple and PowerPoint for Microsoft as well as retriving and sending program information via applications (apps), these can be programmed for automated vision testing utilizing staircase algorithms and binary choice coding. Game-like programs would make eye testing pleasurable for children. With appropriate internet apps, testing is possible around the world.

BRIEF DESCRIPTION OF THE DRAWINGS

The drawings constitute a part of the specifications and include exemplary embodiments to the invention, which may be embodied in various forms. It is to be understood that in some instances various aspects of the invention may be shown exaggerated or enlarged to facilitate an understanding of the invention.

FIG. 21. Stereo viewer with attached iPhone 101

FIG. 22A. Frontal view of iPhone displaying brightness comparison game format

FIG. 22B. View of screen in FIG. 22A seen through stereo viewer 100

FIG. 25A. Frontal view of iPhone displaying visual acuity test for viewing through stereo viewer 100

FIG. 25B. View of screen in FIG. 25A seen through stereo viewer 100

FIG. 26. Frontal view of iPhone displaying visual acuity test for monocular viewing FIG. 27A. Frontal view of iPhone displaying color vision stimuli for viewing through stereo viewer 100, symbols mismatch FIG. 27B. View of screen in FIG. 27A seen through stereo viewer 100

FIG. 28A. Frontal view of iPhone displaying color vision stimuli for viewing through stereo viewer 100, symbols match FIG. 28B. View of screen in FIG. 28A seen through stereo viewer 100

FIG. 29A. Frontal view of iPhone displaying contrast sensitivity stimuli for viewing through stereo viewer 100, symbols mismatch FIG. 29B. View of screen in FIG. 29A seen through stereo viewer 100

FIG. 30A. Frontal view of iPhone displaying contrast sensitivity stimuli for viewing through stereo viewer 100, symbols match FIG. 30B. View of screen in FIG. 30A seen through stereo viewer 100

FIG. 39A. Frontal view of iPhone with vertical alignment gap displaced superiorly FIG. 39B. View of screen in FIG. 39A seen through stereo viewer 100

FIG. 40A. Frontal view of iPhone with vertical alignment gap displaced more superiorly FIG. 40B. View of screen in FIG. 40A seen through stereo viewer 100

FIG. 41A. Frontal view of iPhone with vertical alignment gap displaced inferiorly FIG. 41B. View of screen in FIG. 41A seen through stereo viewer 100

FIG. 42A. Frontal view of iPhone with vertical alignment gap displaced more inferiorly FIG. 42B. View of screen in FIG. 42A seen through stereo viewer 100

FIG. 43A. Frontal view of iPhone with vertical alignment gap displaced even more inferiorly FIG. 43B. View of screen in FIG. 43A seen through stereo viewer 100

FIG. 44A. Frontal view of iPhone with horizontal alignment gap centered

FIG. 44B. View of screen in FIG. 44A seen through stereo viewer 100

FIG. 45A. Frontal view of iPhone with horizontal alignment gap displaced laterally FIG. 45B. View of screen in FIG. 45A seen through stereo viewer 100

FIG. 46A. Frontal view of iPhone with horizontal alignment gap displaced more laterally FIG. 46B. View of screen in FIG. 46A seen through stereo viewer 100

FIG. 47A. Frontal view of iPhone with horizontal alignment gap displaced medially FIG. 47B. View of screen in FIG. 47A seen through stereo viewer 100

FIG. 48A. Frontal view of iPhone with horizontal alignment gap displaced more medially FIG. 48B. View of screen in FIG. 48A seen through stereo viewer 100

FIG. 49A. Frontal view of iPhone with horizontal alignment gap displaced even more medially FIG. 49B. View of screen in FIG. 49A seen through stereo viewer 100

FIG. 50A. Frontal view of iPhone with torsional alignment targets displayed in the horizontal position FIG. 50B. View of screen in FIG. 50A seen through stereo viewer 100

FIG. 51A. Frontal view of iPhone with torsional alignment targers display in the horizontal position FIG. 51B. View of screen in FIG. 51A seen through stereo viewer 100 by a subject having in-cyloversion of the right eye FIG. 51C. Frontal view of iPhone where the torsional target on the screen is rotated counterclockwise to balance and measure in-cycloversion of the right eye as shown in FIG. 51B

FIG. 51D. View of screen in FIG. 51C seen through stereo viewer 100 by a subject having in-cyloversion of the right eye neutralized, the subject now sees only one line in target 184

FIG. 52. Frontal view of iPhone with white background, blue vertical line with gap, and red horizontal line for viewing through complementary color lenses FIG. 53A. Complementary color lenses FIG. 53B. View through the left lens of glasses 157

FIG. 53C. View through the right lens of glasses 157

FIG. 54. Mental image when FIGS. 53B and 53C are fused by a subject having no vertical misalignment.

FIG. 55. Mental image when FIGS. 53B and 53C are fused by a subject having a vertical misalignment, a right hyper deviation

BRIEF DESCRIPTION OF INVENTION

My invention implements binary choice in staircase algorithms to arrive at visual function measurement with minimal or no examiner interaction, with the binary choice made by (1) "YES" or "NO" touch choice or voice command, (2) matching two images, (3) click or no click of a mouse or keyboard, or (4) touch or no touch of the screen. The algorithm may lead to an endpoint presented as a message on the screen to the subject taking the test and/or stored in a file that is available for local or remote analysis. Binary choice self-testing can be utilized on a desktop computer or on a hand-held device such as an iPhone or other programmable devices. The technique is applicable to testing rivalrous brightness comparison, visual acuity, potential vision, color vision, perimetry, and eye alignment as described in the detailed description section below. Image matching as part of binary choice is a powerful method of testing visual acuity and color vision because it provides a completely automated method for testing acuity and color vision and eliminates the testing difficulties associated with illiteracy or language differences and any shape can be used. Binocular vision separation for measuring monocular and binocular functions are disclosed using (1) a stereo viewer and (2) complementary color lenses and color stimuli.

DETAILED DESCRIPTION OF INVENTION

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriate detailed invention, structure or manner.

Figure 1:
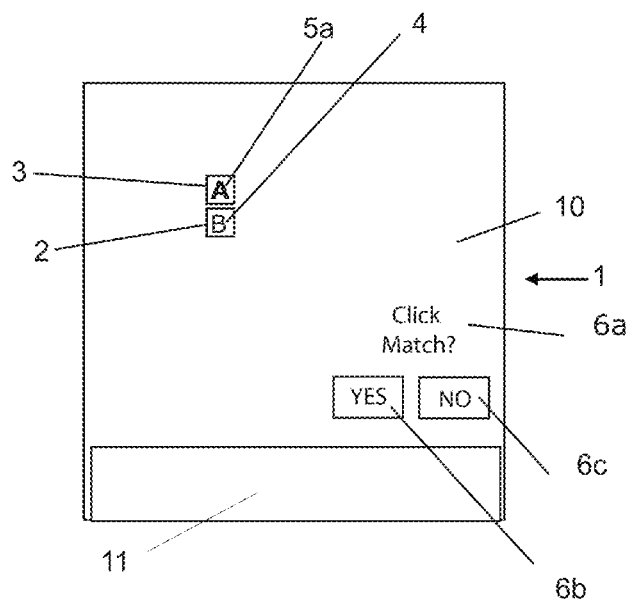
FIG. 1. Frontal view of laptop computer showing mismatched test and reference images and input hyperlinks FIG. 2. Frontal view of laptop computer showing matched test and reference images and input hyperlinks FIG. 3. Sideview of laptop computer FIG. 4. Frontal view of display showing printed overlay and windows in overlay for viewing test and reference electronic images FIG. 5. Sideview showing overlay covering display FIG. 6. Frontal view showing rotatable disc overlay FIG. 7. Sideview showing disc overlay FIG. 8. Cross section view through overlay showing viewing windows in cover FIG. 9. Frontal view of overlay with illuminating attachment FIG. 10. Sideview of overlay showing illuminating attachment housing.
Figure 2:
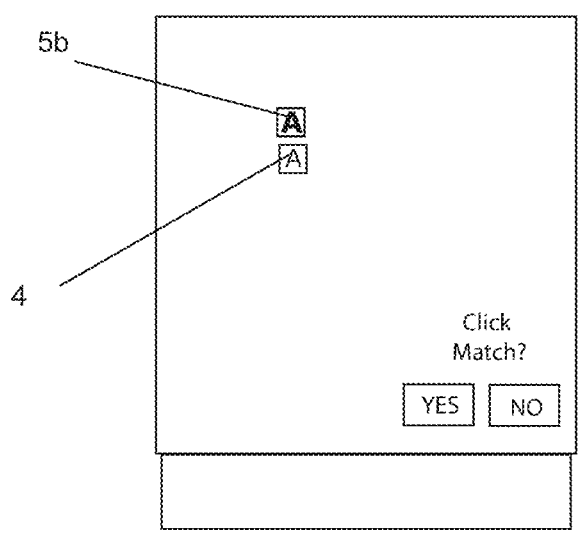
Figure 3:
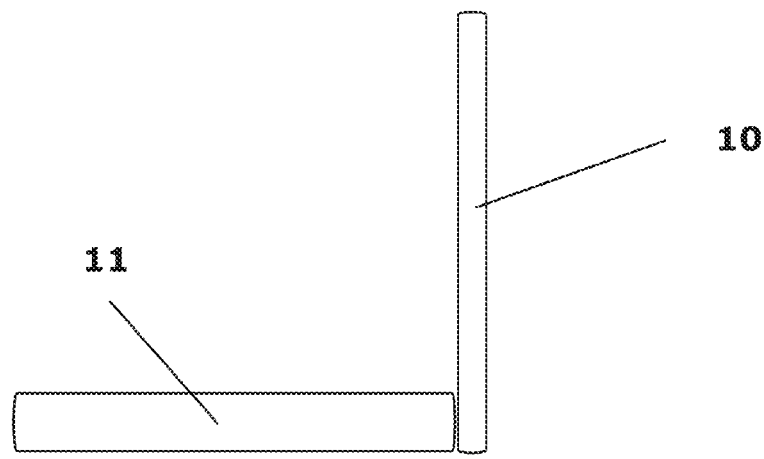

In FIG. 1-3 is computer 1 having a presentation program capable of running macros and programs triggered by a mouse pointer or keystrokes. In this example the computer is a laptop having screen 10 and base 11 with keyboard and mouse controls. Programmed "Click Match" 6*a* is an instructive test box informing the subject to response with a choice of "YES" or "NO", the program will not advance without a response. Text box 6b is hyperlinked to a record file and a "YES" response is recorded when triggered by a mouse click or keystroke which indicates the subject sees the reference image 5a in box 2 and test image 4 in box 3 as identical shapes. If reference image 5a and 4 are seen as differently shaped shapes, "NO" is the correct choice. In FIG. 1 reference image 5a does not match test image 4, the correct binary response is "NO" and test box 6c should be selected. In FIG. 2 reference image 5b and test image 4 match, the correct response is a "YES" and text box 6c should be selected. During testing a specified number of reference images are presented in reference window 3 for comparison to the test image appearing in test window 2, and the subject responses to each reference and test image comparison by activating text box 6b to record a match or 6c to record a mismatch. When a correct match is recorded or when an incorrect match is recorded, a new reference image appears in reference window 3 and the sequence continue through the series of progressive smaller test images until the smallest test image in the progressive series is presented or when a specified number of errors are made as prescribed by the rules of the selected staircase algorithm. The reference images are larger than the test images so that the reference image is accurately and easily recognized when compared to the test image, the size of the test image determines the endpoint. Test images sizes typically range for 20/400 to 20/10.

Figure 4:
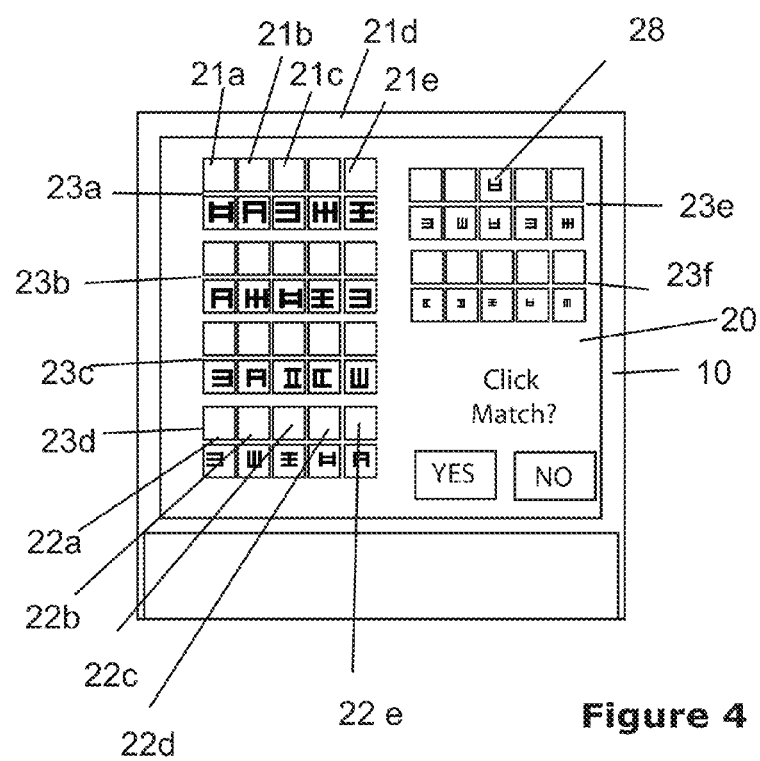
Figure 5:
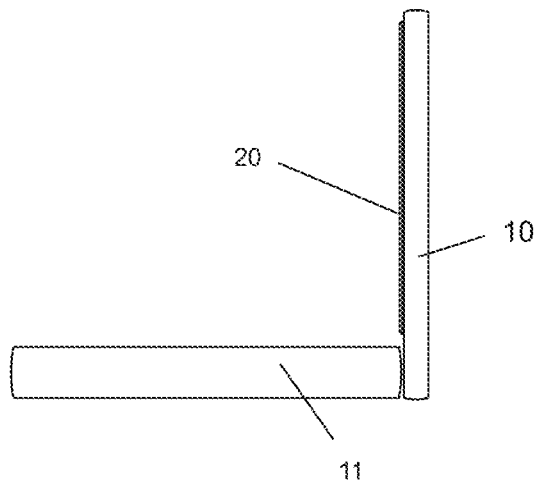

In FIG. 3 is sideview showing screen 10 and keyboard area 11. The computer type may be other than a laptop, for example desktop, tablet, or an enclosed testing device with computer components. Due to the limit of monitor resolution on some models, images cannot be presented in the range from 20/50 to 20/10 letter size when testing at 16 inches or less. The height of a 20/20 size letter is only 0.59 mm. Increasing the subject to monitor distance, images in the range of 20/50 to 20/10 can be presented but long testing distances are not favorable for self-testing techniques where mouse clicking or keyboard strokes are required. In order to test at the standard reading distance of 16 inches or less, a computer monitor overlay with printed high resolution images is needed for less than high resolution monitors when testing fine acuity. In FIG. 4 is shown computer 1 with printed overlay 20 fitted over screen 10. In the overlay there are zones for testing made up of several reference windows and matching test windows. In overlay 20 there are 6 zones, zones 23a-23f with each zone representing a different level of visual acuity. Each zone has 5 reference windows, for example in zone 23a there are reference windows 21a-21e. There are a similar number of test windows in each zone, for example zone 23d has test windows 22a-22e. From zone 23a to 23f the image size in overlay 20 progressively declines. In FIG. 5 reference window 3 and test window 2 are direct windows to the monitor for viewing reference and test images that are of sufficient size to be resolved on the monitor at a near testing distance. Reference image 5b and test image 4 are presented electronically on the monitor. Testing progresses from large to small computer generated reference and test images as depicted in reference window 3 and test window 2 to the acuity level of 20/60 or what ever image size that is clearly seen on that specific monitor. If these images are correctly seen, the program progress to testing with the smaller printed test images by displaying reference images in reference windows above the printed test images from zone 23a through 23f For each zone a series of up to 5 (or other specified number) reference images are sequentially displayed, four images mismatch with the test image and one reference image matches the test image. For progression along the series to occur, the mis- matched images must be correctly noted by activation 6c hyperlink which records "NO". If a mismatching reference image is chosen to match with the test image, an error is recorded and the program progresses to the next smaller line of test images. When the reference image is correctly matched with the test image indicated by activating hyperlink 6b, the result is recorded in a file as a "YES" and the program progress to the next smaller line test images. An example of a reference images is seen in FIGS. 4 as image 28 in zone 23e. In FIG. 5 is sideview showing overlay 20 fitting in front of screen 10.

Figure 6:
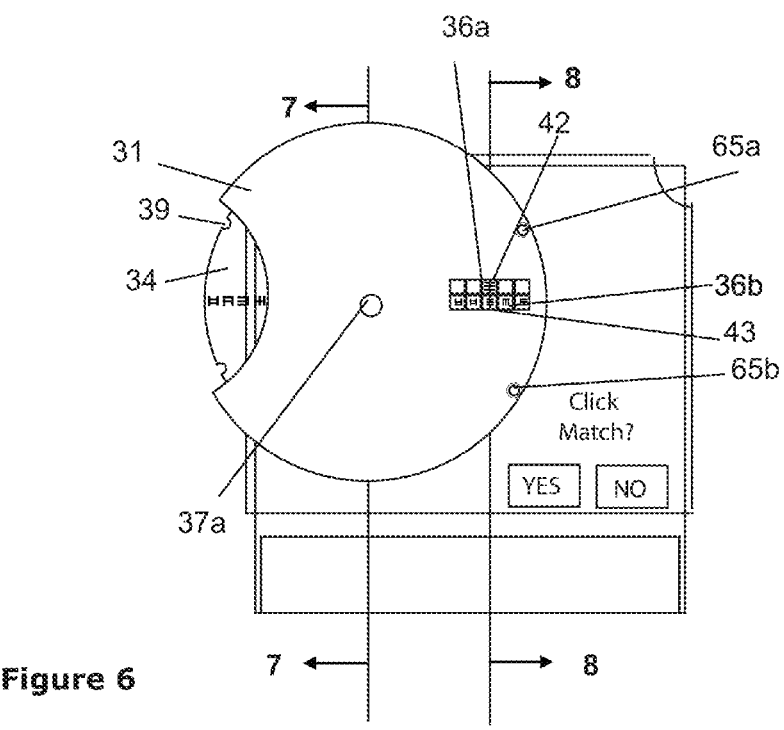
Figure 7:
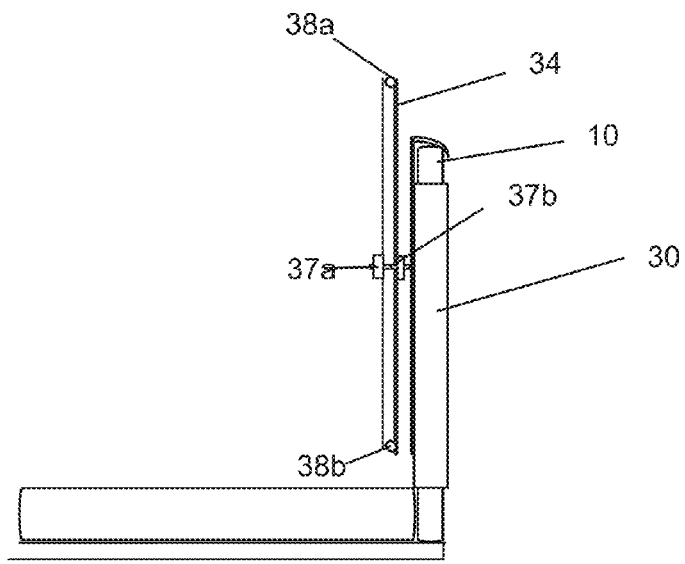
Figure 8:
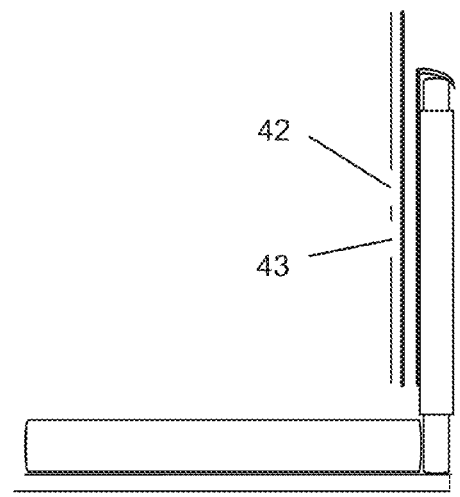
Figure 9:
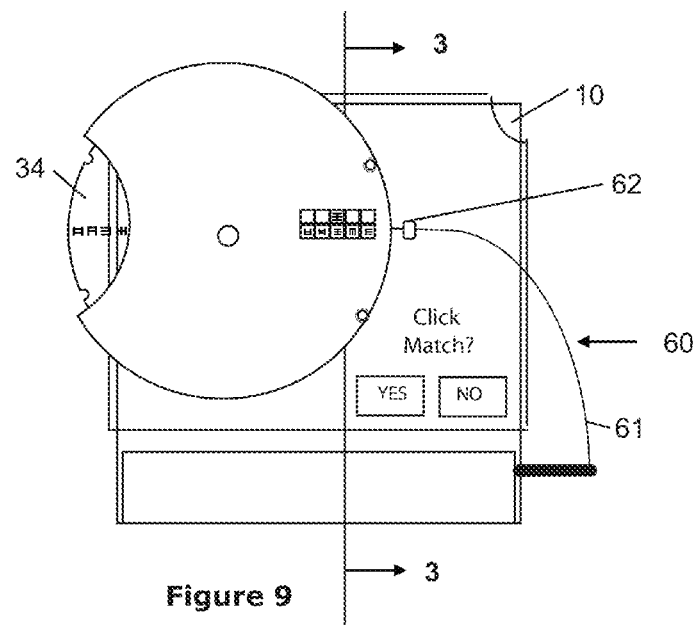

Another embodiment combining tiny printed test images of high resolution and computer generated larger reference images provides means of displaying visual acuity stimuli from 20/400 to 20/10 at 16 inches on a monitor incapable of displaying a 20/10 size letter that is readable by the human eye. Rotable transparent disc 34 printed with high resolution images aligned in rows is illustrated in FIGS. 6-20. In FIG. 6 is chart 34 made up of lines of symbols, with symbols progressive declining in size. Removable cover 31 houses chart wheel 34. Chart 34 rotatable around pivot 37b is attached to support 30, which in turn attaches to and is supported by computer screen 10. The position of cover 31 is stabilized by studs 65a and 65b and secured by fastener 37a. In this example, each line has 5 symbols of identical size. Computer generated reference images appear in test windows which align with test windows located immediately superior to test images, for example reference image 36a is aligned superior to test image 36b as seen in FIG. 6. As chart 34 rotates around pivot 37b in a designated direction so that the image sizes in the series progressively decline. Computer reference image 36a appears in reference window 42 above printed test image 36b in test window 43. In this example, reference images 36a and 36b are identical and if seen correctly by the subject, the correct response would be to click text box 6b, giving a "YES" which hyperlinks matching choice to the file and is stored for later retrieval. FIG. 7 is a cross section through fastener 37a showing pivot 37b attaching to support 30 that fits over screen 10. Support 30 is removed by sliding support up and off of screen 10. In FIG. 7 is illustrated click stops 38a and 38b, which seat into depressions 39 in chart wheel 34 seen in FIG. 6 to cease rotation at points that align test images in test windows 43a-e. The subject at computerized voice commands turns chart wheel 34 manually. FIG. 8 is a cross section through reference window 42 and test window 43 in cover 31. The program algorithm is the same format as described for the first overlay embodiment and providing means for binary choice self-testing.

Figure 10:
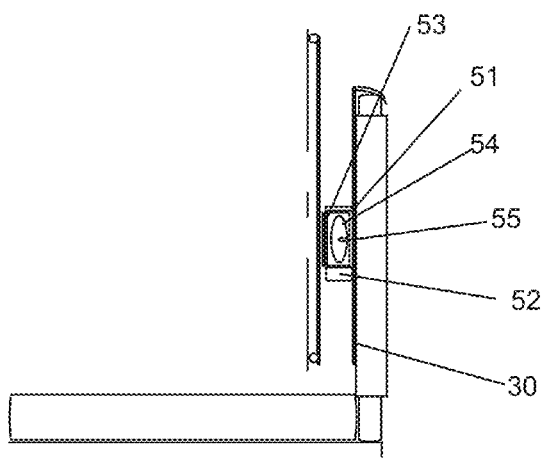

FIGS. 9-20 show my invention having light 60, which provides for brighter illumination of chart wheel 34 than is possible by screen 10 at maximum brightness setting. Visual acuity testing under conditions of very bright chart illumination provides a means of optically penetrating cloudy media of the eye to measure the underlying potential function of macular region of the retina. Testing typically combines bright chart illumination and viewing through a pinhole to reduce optical aberrations and improve vision resolution. Such a method of testing is contained in two of my patents, U.S. Pat. No. 5,398,085 and U.S. Pat. No. 7,857,450. These prior patents do not provide for computerized testing at bright illumination. To provide for potential vision testing at bright illumination, light 60 illuminates printed test images to sufficient brightness. In this example light 60 is powered through USB cable 61 but other power sources could be used. In FIG. 10 components of light 60 are light housing 51, light support 52 which attaches light 60 to support 30, light bulb 55, bulb housing 54, and diffuser 53. The brightness of light 60 can be adjusted by computerized program dimming or by a switch 62 which may have a rheostat control or other means of dimming light bulb 55. The typical laptop screen has a maximim brightness of around 200 cd/m$^2$, whereas the brightness of light 60 is typically in the range of 3000 cd/m$^2$.

Figure 11:
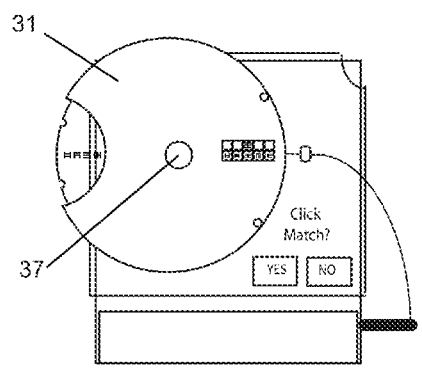
FIG. 11. Frontal view of fully assembled lighted semi-automatic tester
Figure 12:
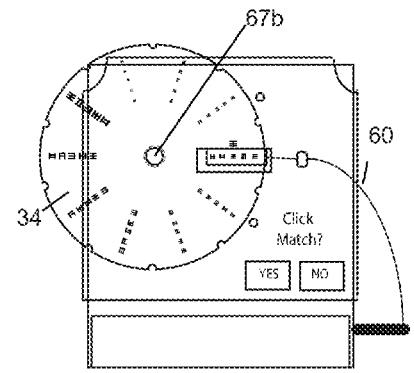
FIG. 12. Frontal view binary choice semi-automatic tester, cover removed
Figure 13:
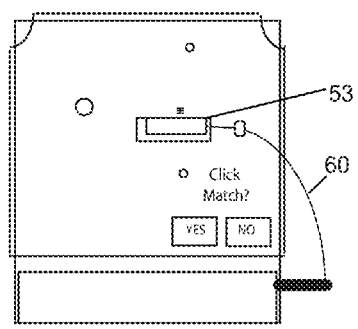
FIG. 13. Frontal view binary choice semi-automatic tester, disc removed
Figure 14:
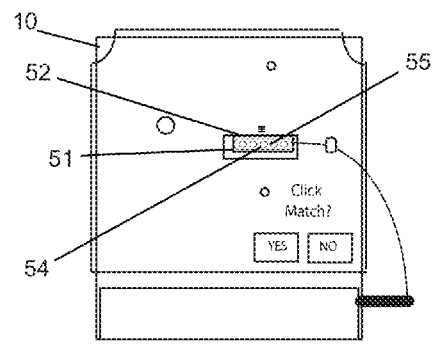
FIG. 14. Frontal view binary choice semi-automatic tester, diffuser removed
Figure 15:
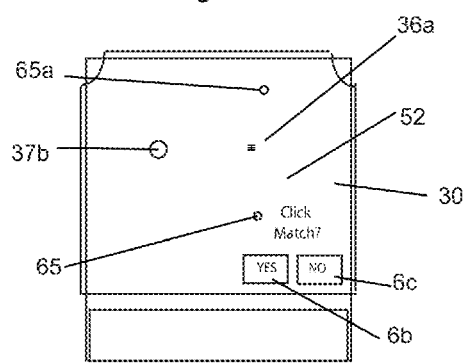
FIG. 15. Frontal view binary choice semi-automatic tester, light removed
Figure 16:
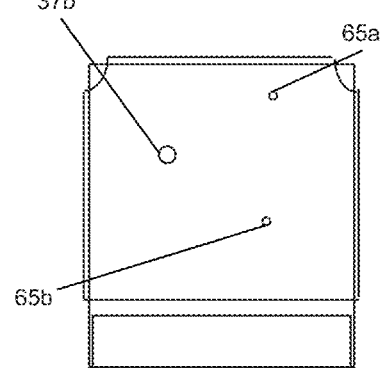
FIG. 16. Frontal view binary choice semi-automatic tester, computer program closed FIG. 17. Frontal view binary choice fully automatic tester FIG. 18. Cross sectional view through the device illustrated in FIG. 17

In FIG. 11 is my fully assembled lighted binary chose semi-automated vision tester. FIGS. 12-16 show various stages of disassembly of my device to better understand the construction of the device. In FIG. 12 cover 31 has been removed by unfastening fastener 37, which fully exposes chart wheel 34. In FIG. 13 chart wheel 34 has been removed by sliding chart wheel 34 off of pivot 67b, which allows access to light 60 and light support 52. FIG. 14 shows diffuser 53 removed and exposure of light housing 51, bulb housing 54 and light bulb 55, and light support 52. In FIG. 15 are seen support 30, computer reference image 36a, and text boxes 6a-6c, pivot 37b, and studs 65a and 65b. Powering down the computer program, removes electronic image 36b and text boxes 6b and 6c, leaving pivot 37b and studs 65a and 65b attached to support 30.

Figure 17:
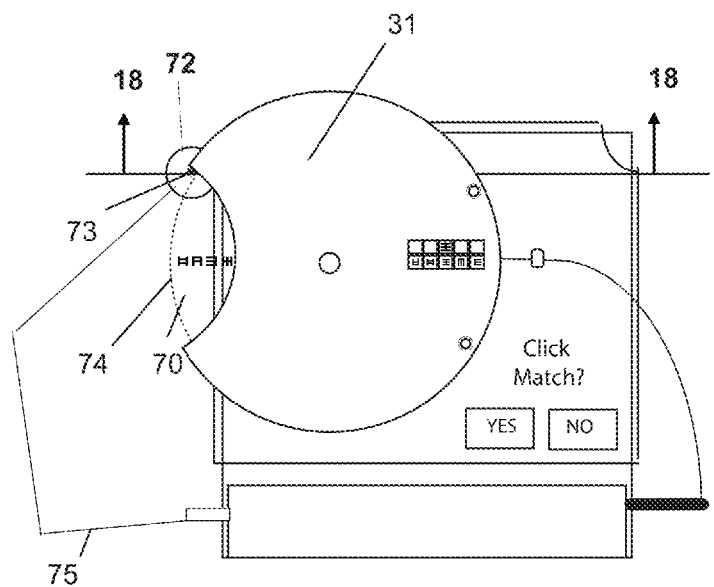
Figure 18:
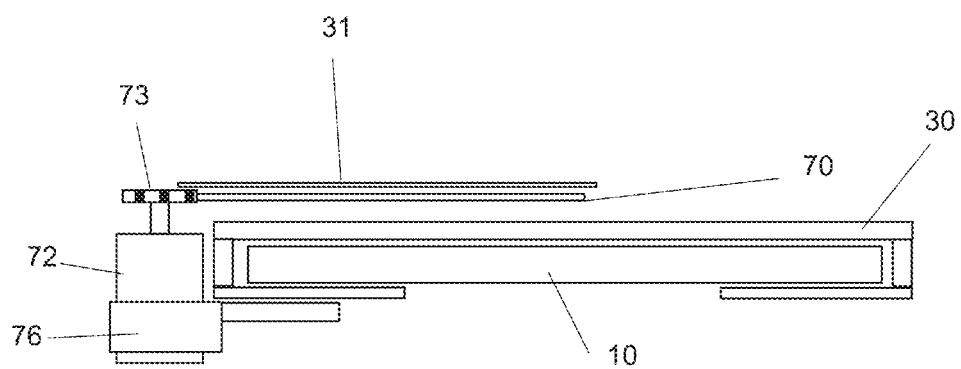

Turn now to FIGS. 17 and 18. To completely automate my invention requires servomotor 72 having gear 73 meshing with cogs 74 on chart wheel 70 with control circuitry being provided via USB cable 75, alternatively an independent controller could be substituted. Utilizing a step rotation program, servomotor 72 can be set to rotate so that the images align precisely in test windows 43a-e. Servomotor 72 is attached to support 30 by bracket 76 as seen in cross section view of FIG. 18.

Figure 19:
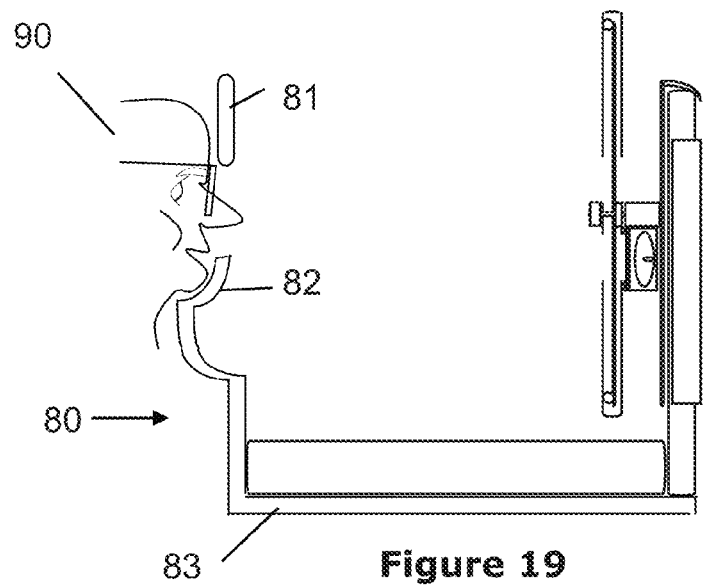
FIG. 19. Sideview of binary choice semi-automatic tester with chin support
Figure 20:
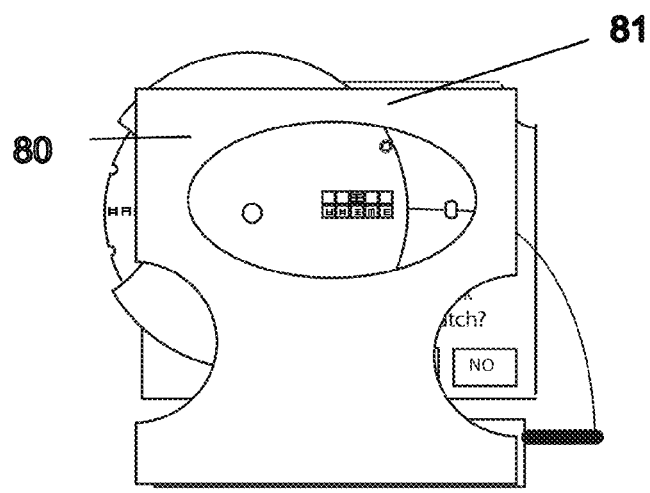
FIG. 20. Frontal view of binary choice semi-automatic tester illustrated in FIG. 19

In order to maintain a fixed testing distance for subject 90, head support 80 may be used which consists of head rest 81, chin rest 82, platform 83 which fits beneath keyboard area 11 as illustrated in FIGS. 19 and 20. Alternatively, the device could be enclosed in a housing and the chin rest could molded into the face of the housing.

Figure 23A:
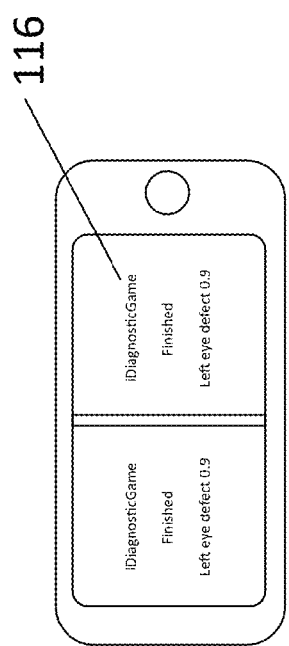
FIG. 23A. Frontal view of iPhone displaying endpoint message
Figure 23B:
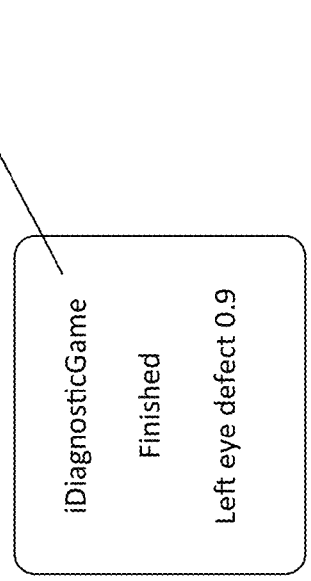
FIG. 23B. View of screen in FIG. 23A seen through stereo viewer 100

With the advent of smart phones and other hand-held computerized devices, eye testing using presentation programs or via apps is now possible. Binary choice self-testing with automated programs for cellular devices makes eye testing possible in the home, schools, and remote areas. The cellular device can be programmed to operate by hyperlinks with the endpoint of displaying a test result to the operator. Data may also be saved in a file locally or remotely. Eye tests using a game format would change eye testing from a boring and stressful activity into a pleasure for children. In FIG. 21 is illustrate stereo-viewer 100 with attached iPhone 101 wherein left eye piece 105 aligns with the left half of screen 103 and right eye piece 106 aligns with the right half of screen 103. Divider 107 isolates the view of screen 103 to right and left sides. In FIG. 22A is the display of iPhone 101 showing screen 103 separated by electronic line image 110 into right and left sides. Depicted in FIG. 22A are electronic images in a game format for the iPhone based on rivalrous brightness comparison principles disclosed in patent application US 20130100400A1 published Apr. 25, 2013. In FIGS. 22A and 22B, rivalrous image pair 112a and 112b are spaceships housing one alien and rivalrous image pair 113a and 113b are spaceships housing two aliens. Each image pair varies in brightness and not form. When said rivalrous image pairs fuse in the brain, images 112 results from the fusion of images 112a and 112b while image 113 results from images 113a and 113b as illustrated in FIG. 22B. In a subject with no brightness sense disparity between the two eyes, fused image 112 appears brighter than image 113 since the average brightness of 112a (100%) and 112b (20%) is brighter than the average brightness of images 113a (20%) and 113b (50%). This is true because images 113a and 112b are of equal brightness (20%) while 112a (100%) is brighter than 113b (50%). Hyperlinks 114a and 114b depicting a spaceship housing one alien are identical and when fused are perceived as image 114. Hyperlinks 115a and 115b of a spaceship housing two aliens are identical and when fused are perceived as image 115 with two aliens. Hyperlinks 114 and 115 are programmed and when touched will elicit a specific advancement in the program which reflects the binary choice made by the subject, ie., the choice of the spaceship with one or two aliens. In this example, the correct choice is 114, which represents brighter fused rivalrous image pair 112, the spaceship with one alien. A typical rivalrous brightness comparison program contains multiple image sets representing brightness disparity from 0 to 2.4 log density units in 0.15 or 0.3 log unit steps of brightness attenuation. Since this is a binocular test, the program presents image sets where the dimmer image is presented to one eye and then the other eye. A staircase algorithm provides a stepwise progression through rivalrous image sets of varying brightness leading to the endpoint of apparent brightness equality of images viewed by the right and left eyes. The typical algorithm contains single and double reversals for choice confirmation. The end result is (1) relative dimness of the right eye, (2) relative dimness of the left eye, (3) no relative difference between the two eye or (4) error. There are built-in error messages when illogical choices are made. The binary choices culminate in an endpoint, which may be revealed to the subject and/or stored in a file for professional analysis. In FIG. 23A is shown an example of the monitor appearance 116 at the conclusion of an iDiagnostic Game test. The subject's perception through stereo viewer 100 is seen in FIG. 23B which concludes that the left eye perceives images dimmer than the right eye by 0.9 log units.

Figure 24A:
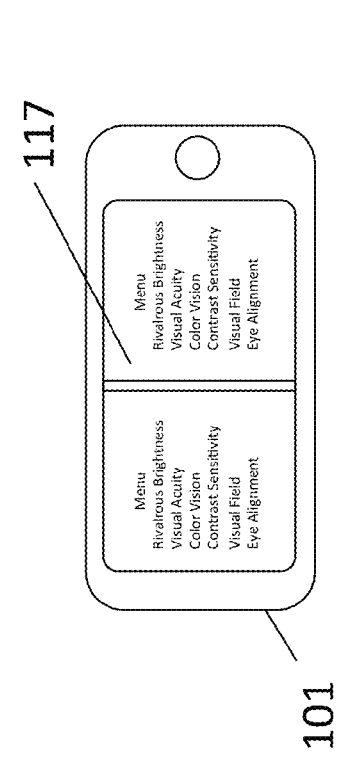
FIG. 24A. Frontal view of iPhone displaying multifunction menu
Figure 24B:
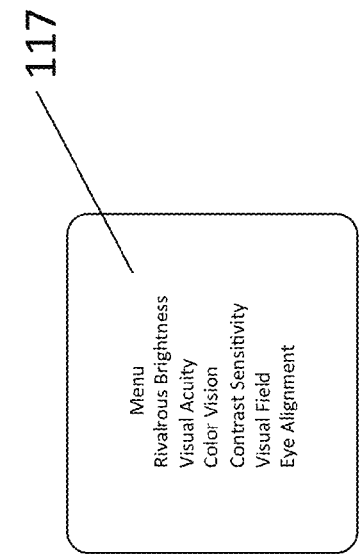
FIG. 24B. View of screen in FIG. 24A seen through stereo viewer 100

In FIG. 24A is menu 117 on iPhone 101 listing hyperlinks to my multifunction electronic automated vision tests using binary choice, each of which will be described herein. Touching the screen or pointing a mouse actives the specified test. Monocular and binocular testing is possible with this method.

Visual acuity testing using my binary choice self-testing not only automates vision testing but also provides symbol matching which allows the use of any symbol, a method that crosses all literacy boundaries. A test symbol of a given size, such as symbol 120 (H) is compared to larger reference 121 (V) as illustrated by iPhone 101 screen in FIGS. 25A and by the subject's view as seen through stereo-viewer 100 in FIG. 25B. When using stereo-viewer 100, the eye not being tested is black to prevent binocualar vision confusing, in FIG. 25A test image 120 and reference image 121 are presented for left eye viewing, the screen viewed by the right eye, side 122b is black. Rather than a stereo viewer; testing may be conducted by occluding the eye not being tested. When testing with one eye patched, the subject views iPhone screen 122 as illustrated in FIG. 26. With either method of viewing, the subject signals a match between test symbol 120 and reference symbol 121 by activating hyperlink 124 or a mismatch by activating hyperlink 123. Each response is recorded and progress continues until errors are made. The right and left eyes are tested separately using either the stereo viewer or patch. Typically, a maximum of 5 reference symbols are sequentially presented to match the test symbol before progressing to the next level of smaller symbols. The endpoint is established using a staircase algorithm with reversals. Selecting the appropriate program the range of vision testing can be specified, typically 20/400 to 20/20 vision range is chosen. With the addition of a pinhole disc over the eye being tested plus adjusting the screen to maximum brightness, potential vision can be tested using methods illustrated by FIGS. 25A, 25B, and 26. The accuracy of potential vision testing with this methods is limited by the maximum brightness of the screen and the degree eye media opacity. The maximum brightness of the iPhone screen is in the range of 500 cd/m² is 5.8 times brighter than the standard reading brightness reading of 85 cd/m².

Another parameter measurable by my invention of binary choice self-testing is color vision as illustrated by iPhone 101 screen in FIGS. 27A and by the subject's view through stereoviewer 100 as seen in FIG. 27B where test color symbol 131 is compared to reference symbol 130a for matching identity. Since symbols 130a and 131 are not identical, the correct response is "NO" match and hyperlink 123 is activated which records the response and trigger the program to replace the reference symbol. If the replacement reference symbol is symbol 130b and identical to test symbol 131 as illustrated in FIGS. 28A and 28B, the correct response is "YES" match and hyperlink 124 is activated which records the response in a file and advances the program to present a new set of test and reference symbols, typically a set of 5 reference symbols are presented for comparison to the test symbol. Test symbols include those for testing (1) color control seen by everyone, (2) blank control, (3) red-green color defect, and (4) blue-yellow color defect. A match is when the test and reference symbols are correctly seen as identical. A mismatch is an error and occurs when (1) identical test and reference symbols are keyed as "NO" match, or (2) when non identical test and reference symbols are keyed as "YES" match. The typical algorithm advances to another set of test and reference symbols when matches and mismatches are chosen. The program continues utilizing a staircase algorithm while recording "YES" and "NO" matches as well as mismatches until color testing is completed.

Another vision parameter measurable by binary choice self-testing is contrast sensitivity. When sine grating are used, the subject signals "YES" when the test and reference targets match in line orientation and signals a "NO" when the test and reference targets mismatch in line orientation. In FIGS. 29A (iPhone 101 screen) and 29b (subject's view through stereo viewer 100) sine grating contrast test symbol 1401 is compared to differently oriented reference symbol 140a. The symbols are not identical as to line orientation and the correct response is to activate hyperlink 123, which signals a "NO" to matching. In FIGS. 30A (iPhone 101 screen) and 30B (subject's view through stereo viewer 100) test symbol 141b and reference 140b are identical and the correct response to matching is a "YES", hyperlink 124 is the correct hyperlink to touch. Typically test and reference symbols are matched 1 out of 5 comparisions. Targets of the same contrast are presented until a "YES" match is correctly made or until a mismatch is made, that is, until non identical symbols are eronously chosen as "YES" match or when identical symbols are eronously chosen as "NO" match. Depending upon the algorithm program, the responses can be saved in a file for analysis or stepwise progress is followed ending is a threshold contrast message presented on the screen. An example of the later stepwise algorithm is as follows: a mismatch at a given contrast level trigger the algorithm to retest at a higher contrast level (easier to see) and progresses again to the contrast level of the original chosen mismatch, if the mismatch is repeated, the algorithm ends by displaying the lowest level of contrast seen correctly. The right and left eyes are tested separately using the stereo-viewer or alternately patching one eye. The program continues utilizing a staircase algorithm with reversals until contrast sensitivity testing is completed. Contrast sensitivity target may be letter, numbers, other symbols, or sine gratings of varying size, typically from 1.5 to 18 cycles per degree Yet another vision parameter measurable by binary choice self-testing is perimetry, visual field testing. Static or kinetic isopters can be utilized. I will describe three embodiments for perimetry applicable to binary choice self-testing with a computer, smart phone, or similar device: (1) using the stereo viewer attachment, (2) using monocular patching, and (3) using complementary color glasses for binocular separation. As per the selected algorithm for any of the embodiments, the program follows a staircase algorithm with retesting for missed or erroneous responses with progression to smaller and/or dimmer isopters as larger or brighter isopters are successfully seen and responses end in a display of the threshold sensitivities of the tested retina with a normal or abnormal optional message displayed or the responses are stored in a file for later analysis. The stimuli can vary in size, intensity, duration, and color as specified in a program.

Figure 32:
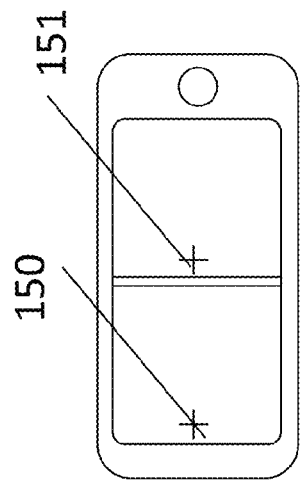
FIG. 32. Frontal view of iPhone display showing left shift of the fixation cross FIG. 33. Frontal view of iPhone display for monocular viewing FIG. 34. Frontal view of iPhone display showing left shift of the fixation cross FIG. 35. Frontal view of iPhone display showing superior shift of the fixation cross FIG. 36A. Frontal view showing fixation cross and red isopter FIG. 36B. Frontal view of left eye image 158 and right eye image 159 as seen through color lenses 157 when screen 101 is white FIG. 37A. Frontal view of left eye image 158 and right eye image 159 as seen through color lenses 157 when screen 101 is black FIG. 37B. Frontal view of left eye image 158 and right eye image 159 as seen through color lenses 157 when screen 101 is black FIG. 38A. Frontal view of iPhone with vertical alignment gap centered FIG. 38B. View of screen in FIG. 38A seen through stereo viewer 100
Figure 31A:
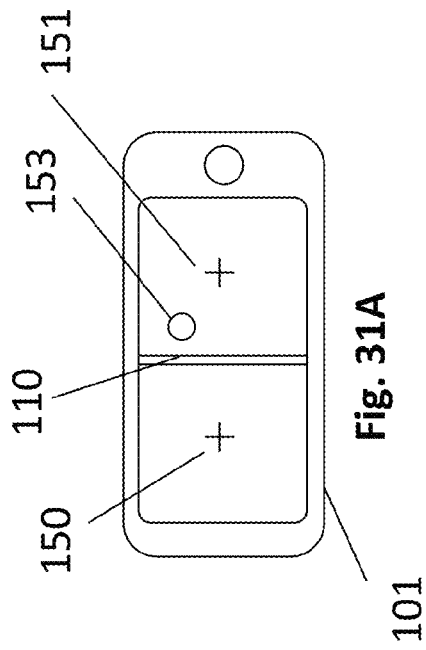
FIG. 31A. Frontal view of iPhone displaying perimetry stimulus for viewing through stereo viewer 100
Figure 31B:
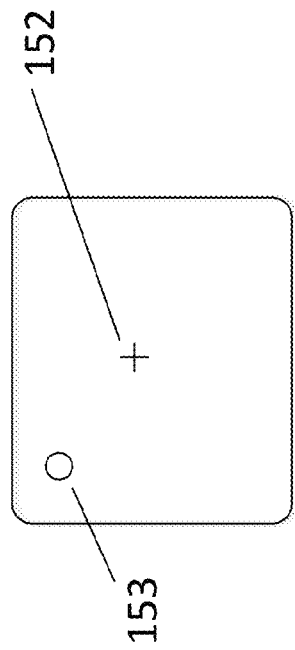
FIG. 31B. View of screen in FIG. 31A seen through stereo viewer 100

Using the stereo viewer attachment embodiment is illustrated in FIG. 31. With the perimetry program loaded, iPhone 101 is displaying screen dividing line 110, fixation cross 150 for left eye viewing, fixation cross 151 for right eye, and round light flash stimulus 153 in the nasal field of the right eye. In FIG. 31B is the view as seen through stereo viewer 101 and shows fixation cross 152 which is the image produced when cross 150 and 151 are fused by the brain. Stimulus 153 is seen only by the right eye. The binary self-testing responses are (1) touching the screen signals a "YES" and (2) no touch within a set time period signals a "NO" response. The stimulus is presented to one eye or the other in a random sequence and the subject responds by touching the screen when and if the stimulus is seen. If the screen is not touched within a set limit of time the program moves to the next appropriate stimulus. Alternately the program emits a sound as a preparatory signal prior to the visual stimulus and allow a time window for a response. As a control, some preparatory sounds are followed by a visual stimulus. The fixation point can be shifted to expand the testable area in any direction, however the extent of the peripheral field testable is limited to one half the size of the display screen. Shifting the fixation point to the left as shown in FIG. 32, expands the nasal field of the left eye and the temporal field of the right eye. The stereo viewer attachment is ideal for testing the central retina or macula for threshold sensitivity. The benefits over monocular perimetry are (1) the eyes can be tested without patching or occluding one observation port, (2) the two eyes can be tested concurrently by randomly alternating test stimuli between the two eyes, and (3) fixation is binocular.

My second embodiment for perimetry using binary choice self-testing is monocular testing where one eye is patched or occluded while the opposite eye is tested. The advantages of monocular perimetry are (1) larger retinal areas can be tested with the small hand-held screen, (2) a stereo viewing adapter is not required, and (3) perimetry can be performed on subject who are unable to fixate binocularily. Seen in FIG. 33 is the screen of iPhone 101 loaded with a staircase algorithm test perimetry where the screen is viewed directly and one eye is patched for testing each monocular visual field. The subject fixates on cross 150 and isopter 153 of a specified size and intensity is presented while the subject views iPhone 101 at a specified distance. To expand the testable area of the retina, fixation cross 150 may be moves in any direction, for example in FIG. 34 cross 150 is moved to the left of the screen which allows for a larger nasal area of testing in the left eye and a larger temporally area of testing in the right eye. Similarly, rotating iPhone 101 so that the long axis of the phone is vertical as shown in FIG. 35 provides for larger superior and inferior field testing. The results may be stored in a file on the phone or stored remotely via the Internet.

My last perimetry embodiment is the use of complementary color lenses and stimuli as illustrated in FIGS. 36-38 where the light from one color isopter is blocked by the lens before one eye and transmitted by the lens before the opposite eye. As with my stereo viewer embodiment for perimetry, a monocular function is being tested with binocular fixation, without a patch, and with random stimulation of the right or left eye. The benefit of complementary color lenses and color stimuli is that a larger visual field is testable with this embodiment. Depending upon the color of the background, the color of the isopter could be the stimulus for the eye behind the lens of the same color as the isopter or could be the stimulus for the eye behind the lens of the complementary color. When the background is dark or black, a stimulus of the same color as the lens is seen as a bright spot and is invisible (light blocked) to the eye behind the lens of the complementary color, however, when the background is white, a stimulus of the complementary color of the lens is seen as a dark or black spot (light blocked) and is invisible to the eye behind the lens of the same color as the stimulus. In FIG. 36A is iPhone 101 displaying black fixation cross 150 and red stimulus 155. In FIG. 36B are red and blue lenses of glasses 157, view 158 as seen through the left blue lens showing blocked red image 155 that appears dark against the white screen background, and view 159 as seen through the right red lens of glasses 157 showing only black cross 150 because red stimulus 155 is fully transmitted which renders it invisible against the bright white background. In FIG. 37A is iPhone screen 101 showing red stimulus 155 on black screen and white fixation cross 150' shifted to the left to increase the field of testing nasally for the left eye and temporally for the right eye. In FIG. 37B are color glasses 157, left eye view 160 as seen through blue left lens showing only white cross 150' with no trace of blocked red stimulus 155 against the black screen background, and right eye view 161 as seen through right red lens showing bright red image 156 against the black screen background. Shown in FIGS. 36A-37B is how the same red stimulus can serve as the stimulus through a red or blue color lens by changing the background color. Theoretically, the transmission values of the stimulus color and complementary color lens should not overlap on the visible light spectrum. Practically, the available color lenses do not completely block the complementary color or allow 100% transmission of the same color and as a result a faint image (residual image) may be visible through the blocking lens when the background is black or visible through the lens of the same color when the background is white. Non-solid color stimuli having white lines or dots in large part overcome the visibility of residual images. The stimulus can vary in duration, brightness, size, and method of appearing (flashing, wiping, etc.).

The last embodiment is a program for measuring eye alignment, a binocular function, using binary choice self-testing. The program measures horizontal, vertical, and torsional alignment of the two eyes. Binocular separation may be by (1) complementary color lenses and color stimuli or (2) a stereo viewer to measure alignment with an electronic programmable device. In FIG. 38A is iPhone 101 loaded with an eye alignment program having horizontal line 170, vertical line 172, gap 173 in vertical line 172, "NO" hyperlinks 123*a* and "Yes" hyperlinks 124*a*. In FIG. 38B is the view of iPhone 101 in FIG. 38A as seen by a subject through stereo viewer 100. A subject having no vertical eye misalignment sees line 170 transecting line 172 through gap 173 as shown in FIG. 38B. Progressing from FIGS. 39A-to 40B gap 173 is increasingly superior to line 172 and should the subject see line 172 bisecting gap 173, a vertical misalignment is diagnosed, in this case a right hyper deviation. In FIGS. 41A-43B, gap 173 is progressively inferior to the line 172 and should a subject see gap 172 bisecting gap 173 when the gap 173 is below line 172, a left hyper deviation is diagnosed. Horizontal deviates are similarly measured as seen in FIGS. 44A-49B. In FIG. 44A vertical line 176 and horizontal line 177 are centered in the right and left halves of the screen of iPhone 101 and gap 178 in centered on line 177. A subject having no horizontal eye misalignment sees line 176 transecting line 177 through gap 178 as shown in FIG. 44B as viewed through stereo viewer 100. Progressing from FIGS. 45A-to 46B gap 178 is increasingly lateral of center and should a subject see line 176 transecting gap 178, a horizontal misalignment is diagnosed, in this case an exo-deviation. In FIGS. 47A-49B gap 178 is increasingly medial of center and should a subject see line 176 transecting gap 178, a horizontal misalignment is diagnosed, in this case an eso-deviation. Torsional misalignment can also be diagnosed using binary choice self-testing on an electronic programmable display. In FIG. 50A is iPhone 101 displaying torsion targets 180 and 181 having horizontal central lines. The visual perception through stereo viewer 100 is seen in FIG. 50B where torsion targets 180 and 181 are superimposed and aligned, an image seen when the subject has no torsional misalignment. In 51*a* are the same torsion targets 180 and 181 but when viewed by an abnormal subject having in-cycloversion of the right eye, torsional target 181 appeared rotated counterclockwise and when fused with torsional target 180 seen by the left eye, composite image 184 having two lines is seen as illustrated in FIG. 51B. To quantify the misalignment a series of targets varying in rotational angle by a specified number of degress are presented to one eye and then the other eye in a staircase program, an example of such rotation is seen in FIG. 52A where the line of torsional target 180 is orientated obliquely. When obliquely orientated targets 180 and 183 appear aligned, as they would to the before mentioned abnormal subject seeing two lines in image 184 of FIG. 51B, the abnormal subject now sees only one line in target 184 and the correct response for this abnormal subject to the audio question, "do you see one line within the circle", is a "Yes" which is triggered by activating hyperlink 124. Following confirmation in the staircase program of the angle of rotation for alignment of the torsional targets the test is completed and the result displayed on the screen, optionally the data is stored locally or remotely.

Complementary color lenses and stimuli can also be used to diagnose and measure eye misalignment as illustrated in FIGS. 52-54B. In this example vertical misalignment is demonstrated, however, the principles apply to horizontal and torsional misalignments. In FIG. 52 is illustrated iPhone 101 with a white background displaying blue vertical line 190 with gap 191, red horizontal line 192, "NO" hyperlink 198 of red font and "Yes" hyperlink 199 of red font. In FIG. 53A are red-blue color glasses having blue lens 193 and red lens 194. FIG. 53B represents the images as seen through blue lens 193 which are horizontal line 192, hyperlink 198 and hyperlink 199 which all appear black due to blue lens 193 blocking transmission of the red color images against the white screen background. FIG. 53C represents vertical line 190 which appears black due to red lens 194 blocking transmission of blue line 190. White gap 191 appearing white. In FIG. 54 is illustrated the mental image resulting from fusion of images illustrated in FIGS. 53B and 53C when the subject has no vertical eye misalignment. In FIG. 55 is illustrated the mental image resulting from fusion of the images of FIGS. 53A and 53B viewed by a subject have a vertical misalignment, a right hyper deviation. A program presents a series of images where gap 192 is displaced specified distances superiorly and inferiorly from the central point of the screen until the subject sees line 191 transecting gap 192, at which time, the correct response for this abnormal subject is a "Yes" and indicated by activating "Yes" hyperlink 199.

The invention claimed is:

1. A method of automated vision testing on a display comprising:
   (a) providing a computer program capable of presenting visual stimuli for monocular or binocular viewing that eliciting specified sensory responses of varying quality and intensity,
   (b) providing an input means which a human can use to make a binary choice between two competing stimuli or distinguish between the presence or absence of a stimulus,
   (c) providing macros that are activated by said input selection that follow a staircase algorithm progressing to threshold endpoint, and
   (d) providing feedback to said human of said threshold.

2. The method of claim 1 further including a file for storing data resulting from said input data selection with said file being retrievable locally or remotely.

3. The method of claim 1 where said display is on a handheld device, such as, a cellular phone, or non-hand held device, such as, a laptop computer.

4. The method of claim 1 where all or part of said computer program resides at a remote site and is communicated to said display via an interne application.

5. The method of claim 1 where said program is an animated game format where said choice changes the animation sequence while following said algorithm.

6. The method of claim 1 where said visual stimuli are displayed for binocular viewing through a stereo viewer for measuring binocular functions of rivalrous brightness comparison and eye alignment or monocular functions of visual acuity, color vision, contrast sensitivity, potential vision, and perimetry.

7. The method of claim 1 where said visual stimuli are complementary colors displayable on a full screen for viewing through complementary color lenses that provides measurement of perimetry and eye alignment.

8. The method of claim 1 where said visual stimuli are displayable for monocular viewing where then one eye is occluded while testing the opposite eye.

9. The method of claim 1 where multiple eye self-tests are listed on said display where each of said self-tests is initiated by a hyperlink activated with a mouse click, a keystroke, or a touch to said display.

\* \* \* \* \*